(12) United States Patent
Mei et al.

(10) Patent No.: US 11,319,563 B2
(45) Date of Patent: May 3, 2022

(54) L-ISOLEUCINE-PRODUCING CORYNEBACTERIUM GLUTAMICUM FERMENTATION MEDIUM AND CULTURE METHOD

(71) Applicant: WUHAN GRAND HOYO CO., LTD., Wuhan (CN)

(72) Inventors: Xuechen Mei, Wuhan (CN); Jiong Wang, Wuhan (CN); Kun Wan, Wuhan (CN); Mengjun Song, Wuhan (CN); Panpan Xing, Wuhan (CN); Haixia Su, Wuhan (CN); Jing Li, Wuhan (CN); Aifu Liu, Wuhan (CN)

(73) Assignee: WUHAN GRAND HOYO CO., LTD., Wuhan (CN)

( * ) Notice: Subject to any disclaimer, the term of this patent is extended or adjusted under 35 U.S.C. 154(b) by 431 days.

(21) Appl. No.: 16/465,838

(22) PCT Filed: Dec. 1, 2017

(86) PCT No.: PCT/CN2017/114198
§ 371 (c)(1),
(2) Date: May 31, 2019

(87) PCT Pub. No.: WO2018/099452
PCT Pub. Date: Jun. 7, 2018

(65) Prior Publication Data
US 2019/0276862 A1 Sep. 12, 2019

(30) Foreign Application Priority Data
Dec. 2, 2016 (CN) .......................... 201611093973.X

(51) Int. Cl.
*C12P 13/06* (2006.01)
*C12N 1/20* (2006.01)

(52) U.S. Cl.
CPC ............... *C12P 13/06* (2013.01); *C12N 1/20* (2013.01); *C12N 2500/05* (2013.01); *C12N 2500/30* (2013.01); *C12N 2500/34* (2013.01); *C12N 2500/38* (2013.01); *C12N 2500/76* (2013.01)

(58) Field of Classification Search
CPC .. C12N 1/20; C12N 2500/05; C12N 2500/30; C12N 2500/34; C12N 2500/38; C12N 2500/76; C12P 13/06
See application file for complete search history.

(56) References Cited

U.S. PATENT DOCUMENTS

| | | | |
|---|---|---|---|
| 3,668,073 A * | 6/1972 | Kurihara ................. | C12P 13/06 435/116 |
| 5,164,307 A | 11/1992 | Yoshihara et al. | |
| 6,107,063 A * | 8/2000 | Moeckel ................. | C12P 13/06 435/116 |
| 2016/0115506 A1 | 4/2016 | Gerstmeir et al. | |
| 2016/0145699 A1* | 5/2016 | Kim ........................ | C12P 13/08 435/116 |

FOREIGN PATENT DOCUMENTS

| | | |
|---|---|---|
| CN | 101235401 A | 8/2008 |
| CN | 101235402 A | 8/2008 |
| CN | 101423851 A | 5/2009 |
| CN | 101457243 A | 6/2009 |
| CN | 101962663 A | 2/2011 |
| CN | 104450815 A | 3/2015 |
| CN | 104480057 A | 4/2015 |
| CN | 104878051 A | 9/2015 |
| CN | 105886431 A | 8/2016 |
| CN | 106701853 A | 5/2017 |
| EP | 1916308 A1 | 4/2008 |
| JP | S6261593 A | 3/1987 |
| JP | S62181791 A | 8/1987 |
| JP | 2016519949 A | 7/2016 |

OTHER PUBLICATIONS

Japanese Office Action issued in Japanese Patent Application No. 2019549626, dated Sep. 16, 2020.
International Search Report and Written Opinion of PCT/CN2017/114198 dated Feb. 28, 2018.
First Office Action and First Search issued in Chinese patent application No. 201611093973.X dated May 22, 2019.
Feng Zhenquan et al., "L-isoleucine Application Status and Prospect", Annual Conference of Biological Fermentation Industry, China, 2013—with English abstract.
Li Guangxi et al., "The advances of studies on fermentation of L-isoleucine", Food and Fermentation Industries, 2006, vol. 32, No. 1, pp. 57-61—with English abstract.
Zou, Huibin et al., "The metabolism and biotechnological application of betaine in microorganism", Appl Microbiol Biotechnol, 2016, vol. 100, p. 3865-3876 (on-line date Mar. 23, 2016).

(Continued)

*Primary Examiner* — Blaine Lankford
(74) *Attorney, Agent, or Firm* — Piloff Passino & Cosenza LLP; Sean A. Passino; Rachel K. Piloff

(57) ABSTRACT

Disclosed is a L-isoleucine-producing *Corynebacterium glutamicum* fermentation medium, comprising a basal medium and a growth factor, wherein the growth factor consists of choline, betaine and vitamin B6, and the contents of each ingredient in the fermentation medium are: 0.2-1 g/L choline, 0.25-0.5 mg/L betaine, and 0.05-0.3 mg/L vitamin B6. Also disclosed is a method for cultivating the L-isoleucine-producing *Corynebacterium glutamicum*, comprising: inoculating the L-isoleucine-producing *Corynebacterium glutamicum* onto the fermentation medium, wherein the volume of the bacteria liquid accounts for 5-20% of the volume of the fermentation medium, adjusting the pH to 6.5-7 with aqueous ammonia, controlling the dissolved oxygen to 30-50%, and fermenting for 25-30 h; then decreasing the dissolved oxygen to 15-25%, and feeding a 50-80% glucose solution into the fermentation broth to control the residual sugar at 3-4%, continuing the fermentation until 60-70 hours, then terminating the fermentation, and controlling the temperature of the overall fermentation process at 29-33° C.

20 Claims, No Drawings

(56) References Cited

OTHER PUBLICATIONS

Xu Jianzhong et al., "An overlooked effect of glycine betaine on fermentation: Prevents caramelization and increases the L-lysine production", Journal of Microbiology and Biotechnology, vol. 24, No. 10, p. 1368-1376 (date Oct. 2014).
Extended European Search Report issued in the counterpart European application No. 17875998.1 dated Nov. 27, 2019.
Japanese Office Action issued in Japanese Patent Application No. 2019549626, dated Mar. 16, 2020.
Masahiko Kisumi, "Studies on the Isoleucine Fermentation," The Journal of Biochemistry, Feb. 1962, pp. 390-399, vol. 52 No. 6.

* cited by examiner

L-ISOLEUCINE-PRODUCING CORYNEBACTERIUM GLUTAMICUM FERMENTATION MEDIUM AND CULTURE METHOD

This application claims the priority of Chinese Patent Application CN201611093973.X, filed on Dec. 2, 2016, the contents of which are incorporated herein by its entirety.

FIELD OF INVENTION

The present invention relates to the field of microbial fermentation, and particularly relates to a fermentation medium and a culture method for L-isoleucine-producing *Corynebacterium glutamicum*.

PRIOR ARTS

In recent years, with the deepening research on the application of L-isoleucine in medical and health care, food processing and feed industry, the market demand for L-isoleucine is growing. Although L-isoleucine has been industrially produced, the current yield is still insufficient. At present, the demand gap for L-isoleucine in China is large, and the annual demand is increasing year by year. The production of L-isoleucine in China faces many problems such as low acid yield, low efficiency of sugar conversion to acid, and low extraction rate of L-isoleucine, etc. The acid production level of L-isoleucine is 25-30 g/L, the extraction rate of L-isoleucine is 65-70%, the highest efficiency of sugar conversion to acid is 18-20%, and the general efficiency of sugar conversion to acid is about 15% in China. In the patent application CN104480057A applied by Jiangnan University in 2014, the efficiency of sugar conversion to acid is only 12.4%; in the patent application CN104878051A applied by Tianjin University of Science and Technology in 2015, the acid production in 5 L fermenter is 40.05 g/L and the efficiency of sugar conversion to acid is 18.7%; while the acid production level of L-isoleucine in Japan is 30-35 g/L, and the extraction rate of L-isoleucine is 70-75% (Li Jing et al., CN104450815A, 2014). It is reported that the acid production level of L-isoleucine is 3.5% and the extraction rate of L-isoleucine is 70% in Ajinomoto (Feng Zhenquan et al., L-isoleucine Application Status and Prospect, 2013). In recent years, the increase in raw materials costs and labor costs both have brought challenges for the production of L-isoleucine.

CONTENT OF THE PRESENT INVENTION

The object of the present invention is to provide a fermentation medium and a culture method for cultivating L-isoleucine-producing *Corynebacterium glutamicum* regarding current issue of low production efficiency of L-isoleucine. By using the fermentation medium and the culture method, the efficiency of sugar conversion to acid can be greatly increased, thereby improving production efficiency of L-isoleucine.

A fermentation medium for cultivating L-isoleucine-producing *Corynebacterium glutamicum* provided herein comprising: a basal medium and a growth factor, the growth factor consists of choline, betaine and vitamin B6, and the contents of growth factor in the fermentation medium are as follows: 0.2-1 g/L of choline, 0.25-0.5 mg/L of betaine, and 0.05-0.3 mg/L of vitamin B6.

Preferably, the basal medium contains the following ingredients, and the contents of each ingredient in the fermentation medium are as follows: 15-25 ml/L of corn steep liquor, 240-300 g/L of glucose, 20-25 g/L of urea, 0.4-0.8 g/L of dipotassium hydrogen phosphate, 0.6-0.8 g/L of magnesium sulfate, 0.2-0.4 mg/L of vitamin B1, 0.015-0.03 mg/L of ferrous sulfate, 1-5 ml/L of corn oil, 2-4 g/L of silk peptide powder, 30-50 ml/L of defoamer.

Further preferably, the contents of each ingredient in the fermentation medium are as follows: 15 ml/L of corn steep liquor, 240 g/L of glucose, 25 g/L of urea, 0.4 g/L of dipotassium hydrogen phosphate, 0.6 g/L of magnesium sulfate, 0.3 mg/L of vitamin B1, 0.015 mg/L of ferrous sulfate, 1 ml/L of corn oil, 0.3 mg/L of betaine, 3 g/L of silk peptide powder, 0.3 mg/L of vitamin B6, 0.5 g/L of choline, 34 ml/L of defoamer.

A culture method for fermenting L-isoleucine-producing *Corynebacterium glutamicum* provided herein comprising: inoculating the colonies of L-isoleucine-producing *Corynebacterium glutamicum* onto the fermentation medium, wherein the volume of bacteria liquid accounts for 5-20% of the volume of the fermentation medium; adjusting the pH to 6.5-7 with aqueous ammonia, maintaining dissolved oxygen at 30-50%, and fermenting for 25-30 hours; then reducing the dissolved oxygen to 15-25%, and feeding a 50-80% of glucose solution into fermentation broth to maintain the residual sugar at 3-4%, continuing the fermentation until 60-70 hours, then terminating the fermentation, and maintaining the temperature of the overall fermentation process at 29-33° C.

Preferably, the culture method for fermenting L-isoleucine-producing *Corynebacterium glutamicum* comprises: inoculating the colonies of L-isoleucine-producing *Corynebacterium glutamicum* onto the fermentation medium of any of claims 1-3, wherein the volume of the bacteria liquid accounts for 10% of the volume of the fermentation medium; adjusting the pH to 6.8 with aqueous ammonia, maintaining the dissolved oxygen at 30%, and fermenting for 26 hours; then reducing the dissolved oxygen to 20%, and feeding a 80% of glucose solution into the fermentation broth to maintain the residual sugar at 3.5%, continuing the fermentation until 70 hours, then terminating the fermentation, and maintaining the temperature of the overall fermentation process at 31° C.

The beneficial effects of the invention are as follows: by adding three growth factors including choline, betaine and vitamin B6 to the culture medium, the invention provides growth factors for *Corynebacterium glutamicum*, maintains the balance of osmotic pressure intracellularly and extracellularly, and promotes the anabolism of amino acids, thereby increasing the yield of L-isoleucine and the efficiency of sugar conversion to acid. The medium and the culture method provided herein have the advantages of high production efficiency, short production cycle and the like.

DETAILED DESCRIPTION OF THE PREFERRED EMBODIMENT

The invention will be described in detail using following embodiments.

Embodiment 1

The fermentation medium for cultivating L-isoleucine-producing *Corynebacterium glutamicum* comprises a basal medium and a growth factor, and the contents of each ingredient in the fermentation medium are as follows:

Basal medium: 15 ml/L corn steep liquor, 240 g/L glucose, 25 g/L urea, 0.4 g/L dipotassium hydrogen phosphate, 0.6 g/L magnesium sulfate, 0.3 mg/L vitamin B1, 0.015 mg/L ferrous sulfate, 1 ml/L corn oil, 3 g/L silk peptide powder, 34 ml/L defoamer.

Growth factors: 0.3 mg/L betaine, 0.5 g/L choline, 0.3 mg/L vitamin B6.

After mixing, it was sterilized at 121° C. for 25 min.

Liquid seed culture medium: 17 g/L Dextrose Monohydrate, 10 ml/L corn steep liquor, 1 g/L urea, 0.5 g/L anhydrous magnesium sulfate, 1 g/L dipotassium hydrogen phosphate, 0.1 g/L silk peptide powder, 0.1 mg/L vitamin B1, 0.1 g/100 ml corn oil, 2 g/100 ml calcium carbonate; adjusted pH 7.0 with NaOH, sterilized at 121° C. for 20 min.

The colonies of L-isoleucine-producing *Corynebacterium glutamicum* on the slope of the test tube was picked and inoculated into a seed culture medium, and cultured in a reciprocating shaker at 31° C. and 105 rpm for 24 hours to obtain a bacterial liquid seed culture.

Culture method for fermenting *Corynebacterium glutamicum* was as follows: the colonies of L-isoleucine-producing *Corynebacterium glutamicum* was inoculated onto the fermentation medium mentioned above, and the volume of the bacterial liquid seed culture accounts for 10% of the volume of the fermentation medium. The pH was adjusted to 6.8 with aqueous ammonia, the dissolved oxygen was maintained at 30%, and the fermentation lasted for 26 hours. Then the dissolved oxygen was reduced to 20%, and an 80% of glucose solution was fed into the fermentation broth to control the residual sugar at 3.5%. The fermentation was continued until 70 hours and then terminated. The temperature of the overall fermentation process was maintained at 31° C.

Embodiment 2

The fermentation medium for cultivating L-isoleucine-producing *Corynebacterium glutamicum* comprises a basal medium and a growth factor, and the contents of each ingredient in the fermentation medium are as follows:

15 ml/L corn steep liquor, 300 g/L glucose, 20 g/L urea, 0.4 g/L dipotassium hydrogen phosphate, 0.6 g/L magnesium sulfate, 0.4 mg/L vitamin B1, 0.03 mg/L ferrous sulfate, 5 ml/L corn oil, 2 g/L silk peptide powder, 50 ml/L defoamer, 0.8 g/L choline, 0.4 mg/L betaine, 0.2 mg/L vitamin B6.

Culture method for fermenting *Corynebacterium glutamicum* was as follows: the colonies of L-isoleucine-producing *Corynebacterium glutamicum* was inoculated onto the fermentation medium, and the volume of the bacteria liquid accounts for 5% of the volume of the fermentation medium. The pH was adjusted to 6.5 with aqueous ammonia, the dissolved oxygen was maintained at 30%, and fermentation lasted for 25 hours. Then the dissolved oxygen was reduced to 15%, and an 80% glucose of solution was fed into the fermentation broth to control the residual sugar at 3%, and the fermentation was continued until 60 hours, and then terminated. The temperature of the overall fermentation process was maintained at 33° C.

Embodiment 3

The fermentation medium for cultivating L-isoleucine-producing *Corynebacterium glutamicum* comprises a basal medium and a growth factor, and the contents of each ingredient in the fermentation medium are as follows:

25 ml/L corn steep liquor, 240 g/L glucose, 25 g/L urea, 0.8 g/L dipotassium hydrogen phosphate, 0.8 g/L magnesium sulfate, 0.2 mg/L vitamin B1, 0.015 mg/L ferrous sulfate, 1 ml/L corn oil, 4 g/L silk peptide powder, 30 ml/L defoamer, 0.3 g/L choline, 0.5 mg/L betaine, 0.1 mg/L vitamin B6.

The culture method for fermenting *Corynebacterium glutamicum* was as follows: the colonies of L-isoleucine-producing *Corynebacterium glutamicum* was inoculated onto the fermentation medium, and the volume of the bacteria liquid accounts for 20% of the volume of the fermentation medium The pH was adjusted to 7 with aqueous ammonia, the dissolved oxygen was controlled at 50%, and the fermentation lasted for 30 hours. Then the dissolved oxygen was reduced to 25%, and a 50% of glucose solution was fed into the fermentation broth to control the residual sugar at 4%, and the fermentation was continued and terminated until 70 hours. The temperature of the overall fermentation process was maintained at 29° C.

Embodiment 4

The fermentation medium for cultivating L-isoleucine-producing *Corynebacterium glutamicum* comprises a basal medium and a growth factor, and the contents of each ingredient in the fermentation medium are as follows:

20 ml/L corn steep liquor, 260 g/L glucose, 23 g/L urea, 0.6 g/L dipotassium hydrogen phosphate, 0.7 g/L magnesium sulfate, 0.3 mg/L vitamin B1, 0.02 mg/L ferrous sulfate, 3 ml/L corn oil, 3 g/L silk peptide powder, 40 ml/L defoamer, 0.6 g/L choline, 0.25 mg/L betaine, 0.05 mg/L vitamin B6.

The culture method for fermenting *Corynebacterium glutamicum* was as follows: the colonies of L-isoleucine-producing *Corynebacterium glutamicum* were inoculated onto the fermentation medium, and the volume of the bacteria liquid accounts for 15% of the volume of the fermentation medium. The pH was adjusted to 6.7 with aqueous ammonia, the dissolved oxygen was maintained at 40%, and the fermentation lasted for 28 hours. Then the dissolved oxygen was reduced to 18%, and a 70% of glucose solution was fed into the fermentation broth to control the residual sugar at 3.8%, and the fermentation was continued and terminated until 64 hours. The temperature of the overall fermentation process was maintained at 30° C.

Embodiment 5

The fermentation medium for cultivating L-isoleucine-producing *Corynebacterium glutamicum* comprises a basal medium and a growth factor, and the contents of each ingredient in the fermentation medium are as follows:

16 ml/L corn steep liquor, 280 g/L glucose, 21 g/L urea, 0.5 g/L dipotassium hydrogen phosphate, 0.7 g/L magnesium sulfate, 0.3 mg/L vitamin B1, 0.02 mg/L ferrous sulfate, 2 ml/L corn oil, 3 g/L silk peptide powder, 40 ml/L defoamer, 0.4 g/L choline, 0.35 mg/L betaine, 0.15 mg/L vitamin B6.

The culture method for the fermentation of *Corynebacterium glutamicum* was as follows: the colonies of L-isoleucine-producing *Corynebacterium glutamicum* were inoculated onto the fermentation medium, and the volume of the bacteria liquid accounts for 12% of the volume of the fermentation medium. The pH was adjusted to 6.8 with aqueous ammonia, the dissolved oxygen was maintained at 30%, and the fermentation lasted for 27 hours. Then the dissolved oxygen was reduced to 20%, and an 80% of glucose solution was fed into the fermentation broth to control the residual sugar at 3.5%, and the fermentation was continued and terminated at 70th hour. The temperature of the overall fermentation process was maintained at 32° C.

EXPERIMENTAL EMBODIMENTS

Comparative Embodiment 1

15 ml/L corn steep liquor, 240 g/L glucose, 25 g/L urea, 0.4 g/L dipotassium hydrogen phosphate, 0.6 g/L magnesium sulfate, 0.3 mg/L vitamin B1, 0.015 mg/L ferrous sulfate, 1 ml/L corn oil, 3 g/L silk peptide powder, 34 ml/L defoamer.
The culture method for fermentation is the same as that in Embodiment 1.

Comparative Embodiment 2

On the basis of Comparative Example 1, 0.3 mg/L of betaine was added. The culture method for fermentation is the same as that in Embodiment 1.

Comparative Embodiment 3

On the basis of Comparative Example 1, 0.5 g/L of choline was added. The culture method for fermentation is the same as that in Embodiment 1.

Comparative Embodiment 4

On the basis of Comparative Example 1, 0.3 mg/L of vitamin B6 was added. The culture method for fermentation is the same as that in Embodiment 1.

The amount of L-isoleucine in fermentation broth was detected (for the detection method, refer to Tang Tao, "Development and Application of HPLC Method for Pre-column Derivatization of Amino Acid", Nanjing University of Science and Technology, 2005.5), the yield of acid was calculated, and the efficiency of sugar conversion to acid was calculated based on the sugar content in the medium. The results are shown in Table 1 below.

TABLE 1

Product yield and the efficiency of sugar conversion to acid of Embodiments 1-5

|  | The yield of L-isoleucine (g/L) | The efficiency of sugar conversion to acid (%) |
| --- | --- | --- |
| Embodiment 1 | 46.7 | 21.4 |
| Embodiment 2 | 42.2 | 18.9 |
| Embodiment 3 | 41.5 | 19.2 |
| Embodiment 4 | 44.8 | 20.6 |
| Embodiment 5 | 44.5 | 21.7 |
| Comparative embodiment 1 | 34.1 | 15.5 |
| Comparative embodiment 2 | 38.7 | 17.9 |
| Comparative embodiment 3 | 37.9 | 16.8 |
| Comparative embodiment 4 | 40.8 | 17.6 |

It can be seen from the above results that the addition of two growth factors into the basal medium can increase the yield of L-isoleucine and the efficiency of sugar conversion to acid, and the increase of yield and conversion efficiency is most obvious when the two growth factors were added simultaneously.

While only specific embodiments of the present invention have been described above, those skilled in the art should understood that these are merely provided for illustration, and many variations or modifications can be made to these embodiments without departing from the principle and spirit of the present invention. Accordingly, the scope of the present invention is defined by the appended claims.

What is claimed is:

1. A fermentation medium for cultivating L-isoleucine-producing *Corynebacterium glutamicum*, comprising: a basal medium and a growth factor, wherein the growth factor consists of choline, betaine and vitamin B6, and the contents of growth factor in the fermentation medium are as follows: 0.2-1 g/L of choline, 0.25-0.5 mg/L of betaine, and 0.05-0.3 mg/L of vitamin B6.

2. The fermentation medium for cultivating L-isoleucine-producing *Corynebacterium glutamicum* of claim 1, wherein the basal medium contains the following ingredients and the contents of each ingredient in the fermentation medium are as follows: 15-25 ml/L of corn steep liquor, 240-300 g/L of glucose, 20-25 g/L of urea, 0.4-0.8 g/L of dipotassium hydrogen phosphate, 0.6-0.8 g/L of magnesium sulfate, 0.2-0.4 mg/L of vitamin B1, 0.015-0.03 mg/L of ferrous sulfate, 1-5 ml/L of corn oil, 2-4 g/L of silk peptide powder, 30-50 ml/L of defoamer.

3. The fermentation medium for cultivating L-isoleucine-producing *Corynebacterium glutamicum* of claim 2, wherein the contents of each ingredient in the fermentation medium are as follows: 15 ml/L of corn steep liquor, 240 g/L of glucose, 25 g/L urea, 0.4 g/L of dipotassium hydrogen phosphate, 0.6 g/L of magnesium sulfate, 0.3 mg/L of vitamin B1, 0.015 mg/L of ferrous sulfate, 1 ml/L of corn oil, 0.3 mg/L of betaine, 3 g/L of silk peptide powder, 0.3 mg/L of vitamin B6, 0.5 g/L of choline, 34 ml/L of defoamer.

4. A culture method for fermenting L-isoleucine-producing *Corynebacterium glutamicum*, comprising: inoculating the colonies of L-isoleucine-producing *Corynebacterium glutamicum* onto the fermentation medium of claim 1 and performing the fermentation.

5. The culture method for fermenting L-isoleucine-producing *Corynebacterium glutamicum* of claim 4, wherein the volume of the bacteria liquid accounts for 10% of the volume of the fermentation medium, adjusting the pH to 6.8 with aqueous ammonia, maintaining the dissolved oxygen at 30%, and fermenting for 26 h; then decreasing the dissolved oxygen to 20%, and feeding a 80% of glucose solution into the fermentation broth to maintain the residual sugar at 3.5%, continuing the fermentation until 70 hours, then terminating the fermentation, and maintaining the temperature of the overall fermentation process at 31° C.

6. The fermentation medium for cultivating L-isoleucine-producing *Corynebacterium glutamicum* of claim 1, comprising 0.3-0.8 g/L of choline.

7. The fermentation medium for cultivating L-isoleucine-producing *Corynebacterium glutamicum* of claim 1, comprising 0.4-0.6 g/L of choline and 0.25-0.35 mg/L of betaine.

8. The fermentation medium for cultivating L-isoleucine-producing *Corynebacterium glutamicum* of claim 1, comprising 0.3, 0.4, 0.5, 0.6 or 0.8 g/L of choline.

9. The fermentation medium for cultivating L-isoleucine-producing *Corynebacterium glutamicum* of claim 1, comprising 0.25, 0.3, 0.35, 0.4 or 0.5 mg/L of betaine.

10. The fermentation medium for cultivating L-isoleucine-producing *Corynebacterium glutamicum* of any of claim 1, comprising 0.05, 0.1, 0.15, 0.2 or 0.3 mg/L of vitamin B6.

11. The fermentation medium for cultivating L-isoleucine-producing *Corynebacterium glutamicum* of claim 1, wherein the fermentation medium comprises: 15 ml/L of corn steep liquor, 300 g/L of glucose, 20 g/L urea, 0.4 g/L of dipotassium hydrogen phosphate, 0.6 g/L of magnesium sulfate, 0.4 mg/L of vitamin B1, 0.03 mg/L of ferrous sulfate, 5 ml/L of corn oil, 0.43 mg/L of betaine, 4 g/L of silk peptide powder, 0.2 mg/L of vitamin B6, 0.5 g/L of choline, 50 ml/L of defoamer.

12. The fermentation medium for cultivating L-isoleucine-producing *Corynebacterium glutamicum* of claim 1, wherein the fermentation medium comprises: 25 ml/L of corn steep liquor, 240 g/L of glucose, 25 g/L urea, 0.8 g/L of dipotassium hydrogen phosphate, 0.8 g/L of magnesium sulfate, 0.2 mg/L of vitamin B1, 0.015 mg/L of ferrous sulfate, 1 ml/L of corn oil, 0.5 mg/L of betaine, 4 g/L of silk peptide powder, 0.1 mg/L of vitamin B6, 0.3 g/L of choline and 30 ml/L of defoamer.

13. The fermentation medium for cultivating L-isoleucine-producing *Corynebacterium glutamicum* of claim 1, wherein the fermentation medium comprises: 20 ml/L of corn steep liquor, 260 g/L of glucose, 23 g/L urea, 0.6 g/L of dipotassium hydrogen phosphate, 0.7 g/L of magnesium sulfate, 0.3 mg/L of vitamin B1, 0.02 mg/L of ferrous sulfate, 3 ml/L of corn oil, 0.25 mg/L of betaine, 3 g/L of silk peptide powder, 0.05 mg/L of vitamin B6, 0.6 g/L of choline, 40 ml/L of defoamer.

14. The fermentation medium for cultivating L-isoleucine-producing *Corynebacterium glutamicum* of claim 1, wherein the fermentation medium comprises: 16 ml/L of corn steep liquor, 280 g/L of glucose, 21 g/L urea, 0.5 g/L of dipotassium hydrogen phosphate, 0.7 g/L of magnesium sulfate, 0.3 mg/L of vitamin B1, 0.02 mg/L of ferrous sulfate, 2 ml/L of corn oil, 0.35 mg/L of betaine, 3 g/L of silk peptide powder, 0.15 mg/L of vitamin B6, 0.4 g/L of choline, 40 ml/L of defoamer.

15. The culture method for fermenting L-isoleucine-producing *Corynebacterium glutamicum* of claim 4, wherein the volume of bacteria liquid accounts for 5-20% of the volume of the fermentation medium; adjusting the pH to 6.5-7 with aqueous ammonia, maintaining the dissolved oxygen at 30-50%, and fermenting for 25-30 h; then reducing the dissolved oxygen to 15-25%, and feeding a 50-80% of glucose solution into the fermentation broth to maintain the residual sugar at 3-4%, continuing the fermentation until 60-70 hours, then terminating the fermentation, and maintaining the temperature of the overall fermentation process at 29-33° C.

16. The culture method for fermenting L-isoleucine-producing *Corynebacterium glutamicum* of claim 15, wherein the volume of bacteria liquid accounts for 10-15% of the volume of the fermentation medium; adjusting the pH to 6.7-6.8 with aqueous ammonia, maintaining the dissolved oxygen at 30-40%, and fermenting for 26-28 h; then reducing the dissolved oxygen to 18-20%, and feeding a 70-80% of glucose solution into the fermentation broth to maintain the residual sugar at 3.5-3.8%, continuing the fermentation until 64-70 hours, then terminating the fermentation, and maintaining the temperature of the overall fermentation process at 30-32° C.

17. The culture method for fermenting L-isoleucine-producing *Corynebacterium glutamicum* of claim 4, wherein the volume of the bacteria liquid accounts for 5% of the volume of the fermentation medium, adjusting the pH to 6.5 with aqueous ammonia, maintaining the dissolved oxygen at 30%, and fermenting for 25 h; then decreasing the dissolved oxygen to 15%, and feeding a 80% of glucose solution into the fermentation broth to maintain the residual sugar at 3%, continuing the fermentation until 60 hours, then terminating the fermentation, and maintaining the temperature of the overall fermentation process at 33° C.

18. The culture method for fermenting L-isoleucine-producing *Corynebacterium glutamicum* of claim 4, wherein the volume of the bacteria liquid accounts for 20% of the volume of the fermentation medium, adjusting the pH to 7 with aqueous ammonia, maintaining the dissolved oxygen at 50%, and fermenting for 30 h; then decreasing the dissolved oxygen to 25%, and feeding a 50% of glucose solution into the fermentation broth to maintain the residual sugar at 4%, continuing the fermentation until 70 hours, then terminating the fermentation, and maintaining the temperature of the overall fermentation process at 29° C.

19. The culture method for fermenting L-isoleucine-producing *Corynebacterium glutamicum* of claim 4, wherein the volume of the bacteria liquid accounts for 15% of the volume of the fermentation medium, adjusting the pH to 6.7 with aqueous ammonia, maintaining the dissolved oxygen at 40%, and fermenting for 28 h; then decreasing the dissolved oxygen to 18%, and feeding a 70% of glucose solution into the fermentation broth to maintain the residual sugar at 3.8%, continuing the fermentation until 64 hours, then terminating the fermentation, and maintaining the temperature of the overall fermentation process at 30° C.

20. The culture method for fermenting L-isoleucine-producing *Corynebacterium glutamicum* of claim 4, wherein the volume of the bacteria liquid accounts for 12% of the volume of the fermentation medium, adjusting the pH to 6.8 with aqueous ammonia, maintaining the dissolved oxygen at 30%, and fermenting for 27 h; then decreasing the dissolved oxygen to 20%, and feeding a 80% of glucose solution into the fermentation broth to maintain the residual sugar at 3.5%, continuing the fermentation until 70 hours, then terminating the fermentation, and maintaining the temperature of the overall fermentation process at 32° C.

* * * * *